(12) United States Patent
Liew et al.

(10) Patent No.: US 7,329,699 B2
(45) Date of Patent: Feb. 12, 2008

(54) COMPOSITION CONTAINING OIL, STRUCTURING POLYMER, AND COATED SILICONE ELASTOMER, AND METHODS OF MAKING AND USING THE SAME

(75) Inventors: Terry Van Liew, Cranford, NJ (US); Shaoxing Lu, Plainsboro, NJ (US)

(73) Assignee: L'Oreal, Paris (FR)

( * ) Notice: Subject to any disclaimer, the term of this patent is extended or adjusted under 35 U.S.C. 154(b) by 475 days.

(21) Appl. No.: 10/617,048

(22) Filed: Jul. 11, 2003

(65) Prior Publication Data

US 2005/0009989 A1   Jan. 13, 2005

(51) Int. Cl.
*A61Q 3/00* (2006.01)
*A61Q 5/00* (2006.01)
*C08G 77/04* (2006.01)

(52) U.S. Cl. ............... 524/261; 524/267; 524/268; 524/269; 524/474; 524/476; 524/481; 524/484; 524/491; 524/500; 524/502; 524/504; 524/506; 524/538; 524/539; 524/540; 523/201; 523/203; 523/205; 523/206; 523/209; 523/212; 523/216; 8/405; 8/552; 132/202; 424/70.12

(58) Field of Classification Search .............. 524/261, 524/267, 268, 269, 474, 476, 481, 484, 491, 524/500, 502, 504, 506, 539, 540, 538; 523/201, 523/203, 205, 206, 209, 212, 216; 8/405, 8/552; 132/202; 424/70.12
See application file for complete search history.

(56) References Cited

U.S. PATENT DOCUMENTS

| | | |
|---|---|---|
| 2,823,195 A | 2/1958 | Shorr et al. |
| 2,823,218 A | 2/1958 | Speier et al. |
| 3,723,566 A | 3/1973 | Thompson et al. |
| 4,322,400 A | 3/1982 | Yuhas |
| 4,822,852 A | 4/1989 | Wittmann et al. |
| 5,262,505 A | 11/1993 | Nakashima et al. |
| 5,407,986 A | 4/1995 | Furukawa et al. |
| 5,412,004 A | 5/1995 | Tachibana et al. |
| 5,473,041 A | 12/1995 | Itoh |
| 5,567,428 A | 10/1996 | Hughes |
| 5,725,882 A | 3/1998 | Kuman et al. |
| 5,837,223 A | 11/1998 | Barone et al. |
| 5,874,069 A | 2/1999 | Mendolia et al. |
| 5,919,441 A | 7/1999 | Mendolia et al. |
| 5,969,172 A | 10/1999 | Nye |
| 5,981,680 A | 11/1999 | Petroff et al. |
| 5,985,297 A | 11/1999 | Mellul et al. |
| 6,045,782 A | 4/2000 | Krog et al. |
| 6,051,216 A | 4/2000 | Barr et al. |
| 6,060,072 A | 5/2000 | Konik et al. |
| 6,103,250 A | 8/2000 | Brieva et al. |
| 6,177,091 B1 | 1/2001 | Bara et al. |
| 6,353,076 B1 | 3/2002 | Barr et al. |
| 6,362,287 B1 | 3/2002 | Chorvath et al. |
| 6,362,288 B1 | 3/2002 | Brewer et al. |
| 6,376,078 B1 * | 4/2002 | Inokuchi ............... 428/403 |
| 6,423,324 B1 | 7/2002 | Murphy et al. |
| 6,426,062 B1 | 7/2002 | Chopra et al. |
| 6,451,295 B1 | 9/2002 | Cai et al. |
| 6,503,632 B1 | 1/2003 | Hayashi et al. |
| 6,524,598 B2 | 2/2003 | Sunkel et al. |
| 6,541,017 B1 | 4/2003 | Lemann et al. |
| 6,569,955 B1 | 5/2003 | Brewer et al. |
| 6,916,464 B2 * | 7/2005 | Hansenne et al. ......... 424/59 |
| 2002/0028223 A1 | 3/2002 | Vatter et al. |
| 2002/0048557 A1 | 4/2002 | Cai et al. |
| 2002/0051758 A1 | 5/2002 | Cai et al. |
| 2003/0068348 A1 | 4/2003 | Ferrari et al. |
| 2003/0072730 A1 | 4/2003 | Tournilhac |
| 2003/0082129 A1 | 5/2003 | Buckingham et al. |
| 2003/0170188 A1 | 9/2003 | Ferrari et al. |
| 2003/0228333 A1 | 12/2003 | Fecht et al. |
| 2003/0232030 A1 | 12/2003 | Lu et al. |
| 2003/0235548 A1 | 12/2003 | Lu |
| 2003/0235552 A1 | 12/2003 | Yu |
| 2003/0235553 A1 | 12/2003 | Lu et al. |
| 2004/0001799 A1 | 1/2004 | Lu et al. |
| 2004/0115153 A1 | 6/2004 | Yu |
| 2004/0115154 A1 | 6/2004 | Yu |

(Continued)

FOREIGN PATENT DOCUMENTS

CN   1386489   12/2002

(Continued)

OTHER PUBLICATIONS

Dow Corning® 2-8178 Gellant, Ref. No. 27-1055-01; Product Information Personal Care; 6pp.; Aug. 2002.
Shin-Etsu Silicones for Personal Care: Product Brochure, KSP-200○300 "Hybrid Silicone Powders containing Fluoroalkyl or Phenyl group for Personal Care";12pp., 2001.
Shin-Etsu Silicones for Personal Care; Product Brochure, KSP-100○102○103○104○105; "Hybrid Silicone Powders for Personal Care"; 8pp.; 2001.
Dow Corning® 2-8178 Gellant, Ref. No. 27-1055-01; 35pp., Aug. 2002.
Dow Corning® 2-8178 Gellant, Ref. No. 27-1055-01, Aug. 2002, 35 pp.
Dow Corning® 2-8178 Gellant, Product Information Personal Care, 6 pp., Aug. 13, 2002.

(Continued)

*Primary Examiner*—Ana Woodward
(74) *Attorney, Agent, or Firm*—Oblon, Spivak, McClelland, Maier & Neustadt, P.C.

(57) ABSTRACT

The invention relates to a composition, preferably a care and/or treatment and/or make-up composition for keratin and keratinous materials in general (including the skin, hair, nails, scalp, and/lips of human beings, keratinous fibers, etc.), containing an oil, a structuring polymer and a coated silicone elastomer. Preferably, the compositions of the invention are anhydrous.

37 Claims, No Drawings

U.S. PATENT DOCUMENTS

| | | |
|---|---|---|
| 2004/0120912 A1 | 6/2004 | Yu |
| 2004/0126336 A1 | 7/2004 | Hansenne et al. |
| 2004/0170586 A1 | 9/2004 | Ferrari et al. |
| 2004/0180032 A1 | 9/2004 | Manelski et al. |
| 2004/0197285 A1 | 10/2004 | Van Dort |
| 2004/0223936 A1 | 11/2004 | Fecht et al. |
| 2005/0009989 A1 | 1/2005 | Liew et al. |
| 2005/0020769 A1 | 1/2005 | Lu et al. |
| 2005/0089492 A1 | 4/2005 | Lu et al. |
| 2005/0158260 A1 | 7/2005 | Ferrari et al. |

FOREIGN PATENT DOCUMENTS

| | | |
|---|---|---|
| EP | 0 377 447 A2 | 7/1990 |
| EP | 0 594 285 A2 | 4/1994 |
| EP | 0 693 517 A1 | 1/1996 |
| EP | 0 923 928 | 6/1999 |
| EP | 1 048 686 | 11/2000 |
| EP | 1 068 856 | 1/2001 |
| EP | 1 266 647 | 12/2002 |
| EP | 1 266 648 | 12/2002 |
| FR | 2 765 800 | 1/1999 |
| GB | 134 8783 | 3/1974 |
| WO | WO 97/36572 | 10/1997 |
| WO | WO 97/36573 | 10/1997 |
| WO | WO 99/47111 | 1/1999 |
| WO | WO 99/06473 | 2/1999 |
| WO | WO 01/09239 A1 | 2/2001 |
| WO | WO 01/97758 A2 | 12/2001 |
| WO | WO 02/17870 A2 | 3/2002 |
| WO | WO 02/17871 A2 | 3/2002 |
| WO | WO 02/089760 A1 | 11/2002 |
| WO | WO 03/013447 A2 | 2/2003 |
| WO | WO 03/105788 A2 | 6/2003 |
| WO | WO 03/101412 A2 | 12/2003 |
| WO | WO 2004/054523 | 7/2004 |
| WO | WO 2004/054524 | 7/2004 |

OTHER PUBLICATIONS

Shin-Etsu Silicones for Personal Care; Product Brochure, KSP-100•101•102•103•104•105 "Hybrid Silicone Powders for Personal Care" 2000.

Shin-Etsu Silicones for Personal Care; Product Brochure, KSP-200•300 "Hybrid Silicone Powders containing Fluoroalkyl or Phenyl group for Personal Care" 2001.

English Language Derwent Abstract of EP 0 923 928, Jun. 23, 1999.
English Language Derwent Abstract of EP 1 068 856, Jan. 17, 2001.
English Language Derwent Abstract of FR 2 765 800, Jan. 15, 1999.

* cited by examiner

COMPOSITION CONTAINING OIL, STRUCTURING POLYMER, AND COATED SILICONE ELASTOMER, AND METHODS OF MAKING AND USING THE SAME

SUMMARY OF THE INVENTION

The present invention relates to a composition, preferably a care and/or treatment and/or make-up composition for keratin and keratinous materials (including the skin, hair, nails, scalp, and/lips of human beings, keratinous fibers, etc.), the invention composition comprising an oil, a structuring polymer, and a coated silicone elastomer. Preferably, the compositions of the invention are anhydrous. Methods of making and using this composition also make up a part of the invention.

DETAILED DESCRIPTION OF THE INVENTION

In this application, where a component of the invention is noted, whether in the specification or claims, more than one of such components may be present therein. That is, mixtures of invention components may be present in invention compositions. The term "and/or" means either one alone or both together. The term "stable" refers to a composition, in particular a stick, that is hard, and does not collapse over time at room temperature (25° C.) and at 45° C. for at least 1 month. The expression "at least one" means one or more and thus includes individual components as well as mixtures/combinations. The expression "polymer" means a compound having at least two repeating units, preferably at least three repeating unit, more preferably at least ten repeating units.

Preferably, the invention composition is stable, and may be in any form such as that of a tube or stick, a paste, etc. In a preferred embodiment the invention composition is in the general form of a rigidified or solid gel that is reversible thermally and/or upon the application of shear. Such structured, e.g., gelled and/or rigidified, oil-containing compositions are useful in cosmetic and/or dermatological products; this is especially the case in solid compositions such as deodorants, lip balms, lipsticks, concealer products, eye shadows and cast foundations. While not bound by theory, it is believed that the structuring polymer structures the oil, making it possible in particular to limit its exudation (or syneresis) from solid compositions, particularly in hot and humid areas and, furthermore, after deposition on the skin or the lips, to limit the migration of this phase into wrinkles and fine lines, a characteristic particularly desirable in a lipstick or eye shadow. The reason for this is that considerable migration of the oil phase, particularly when it is charged with coloring agents, may lead to an unpleasant appearance around the lips and the eyes, making wrinkles and fine lines particularly prominent. Consumers often state this migration as being a major drawback of conventional lipsticks and eye shadows. The term "migration" means movement of the composition beyond its initial site of application.

One preferred embodiment of the invention is a composition, more preferably a care and/or make-up and/or treatment composition for the skin and/or the lips of the face and/or for superficial body growths, i.e., keratinous materials, such as nails or keratinous fibers, which provides good properties such as good sensory qualities, good migration properties, etc.

The inventors have found, surprisingly, that compositions comprising at least one structuring polymer, at least one oil (the oil making up some or all of a fatty phase sometimes referred to herein as a liquid fatty phase) and at least one coated silicone elastomer provides a product that is useful in, e.g., cosmetic and dermatological areas, for example providing a product with noteworthy cosmetic properties.

The invention applies not only to make-up products for the lips, such as lipsticks, lip glosses and lip pencils, but also to care and/or treatment products for the skin, including the scalp, and for the lips, such as antisun care products for the human face, the body or the lips, such as in stick form, make-up removing products for the skin of the face and body, make-up products for the skin, both of the human face and body, such as foundations optionally cast in stick or dish form, concealer products, blushers, eyeshadows, face powders, transfer tattoos, body hygiene products (i.e., products which do not relate to the care, make-up, or treatment of keratin materials) such as deodorant, e.g., in stick form, shampoos, conditioners and make-up products for the eyes such as eyeliners, eye pencils and mascaras, e.g., in cake form, as well as make-up and care products for superficial body growths, for instance keratinous fibers such as the hair, the eyelashes, and the eyebrows or nails. Overall, it is of course preferred that the invention composition as a whole constitute a physiologically acceptable medium, in view of its usefulness in the cosmetic area.

The composition of the invention can also be in the form of a paste, a solid or a more or less viscous cream. It can be a single or multiple emulsion, such as an oil-in-water or water-in-oil emulsion or an oil-in-water-in-oil emulsion, or a water-in-oil-in-water emulsion, or a rigid or soft gel containing an oily continuous phase. For example, the liquid fatty phase can be the continuous phase of the composition. In one embodiment, which is highly preferred herein, the composition is anhydrous. In another embodiment, the composition is in a form cast as a stick or in a dish, for example solid, and further example, in the form of an oily rigid gel, such as an anhydrous gel, e.g., an anhydrous stick. In a further embodiment, the composition is in the form of an opaque or translucent rigid gel (depending on the presence or absence of pigments), and in a specific example, the liquid fatty phase forms the continuous phase. In one embodiment, the composition is chosen from molded and poured sticks.

Structuring Polymer

In the composition according to the present invention, the structuring polymer preferably represents 0.1 to 99% by weight, more likely 0.5 to 80% by weight, more preferably 2 to 60% by weight, even more preferably 5 to 40% by weight, of the total weight of the composition. More or less may be used if desired, and these ranges include all values and subranges therebetween as if specifically written out.

Preferred structuring polymers useful herein are referred to as DC 8178 and DC 8179 from Dow Corning, which are Nylon-611/Dimethicone Copolymers, which optionally may be present in or with PPG-3 Myristyl Ether. The molecular weight of these copolymers may vary from, e.g., about 60,000-150,000, 65,000-140,000, etc., Daltons. Preferred materials have molecular weights in the lower end of these ranges, for example 60,000-70,000, including 62,000, 68,000, etc. Dow Product Information regarding these copolymers is incorporated herein by reference. Preferably, the structure is as follows:

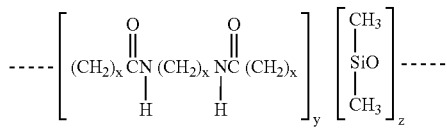

where x, y, and z are appropriate to meet the molecular weight. Optionally, x, which may be the same or different, is 1-200, preferably 1-100 including 10, 20, 30, 40, etc., including all values between all ranges, and the ratio y/z optionally varies from 0.01 to 100, more preferably 1-10, including all values between all ranges.

Another preferred structuring polymer useful herein is a polymer (homopolymer or copolymer) preferably having a weight-average molecular weight ranging from 500 to 500 000, comprising at least one moiety comprising:
- at least one polyorganosiloxane group, preferably having from 1 to 1 000 organosiloxane units in the chain of the moiety or in the form of a graft, and
- at least two groups, which may be the same or different, capable of establishing hydrogen interactions, chosen from ester, amide, sulphonamide, carbamate, thiocarbamate, urea, urethane, thiourea, oxamido, guanamido and biguanidino groups, and combinations thereof, the polymer preferably being solid at 25° C. and soluble in the fatty phase at a temperature of from 25 to 250° C. The invention structuring polymer in general is preferably solid at room temperature (25° C.) and atmospheric pressure (760 mm Hg) and soluble in the oil and/or liquid fatty phase at a temperature of from 25 to 250° C.

Polymers useful as structuring agents in the composition of the invention include polymers of the polyorganosiloxane type such as those described in documents U.S. Pat. Nos. 5,874,069, 5,919,441, 6,051,216, and U.S. Pat. No. 5,981,680, all incorporated herein by reference. Also preferred are polymers from Dow Corning known as DC8178 and 8179, the product descriptions of these materials being incorporated herein by reference (see above).

Useful structuring polymers further include polymers comprising at least one moiety corresponding to the formula:

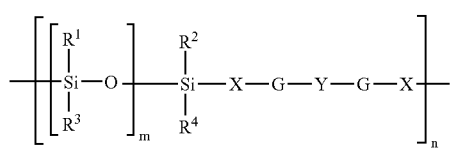

in which:
1) $R^1$, $R^2$, $R^3$ and $R^4$, which may be identical or different, represent a group chosen from:
   - linear, branched or cyclic, saturated or unsaturated, $C_1$ to $C_{40}$ hydrocarbon-based groups, possibly containing in their chain one or more oxygen, sulphur and/or nitrogen atoms, and possibly being partially or totally substituted with fluorine atoms,
   - $C_6$ to $C_{10}$ aryl groups, optionally substituted with one or more $C_1$ to $C_4$ alkyl groups,
   - polyorganosiloxane chains possibly containing one or more oxygen, sulphur and/or nitrogen atoms;

2) the groups X, which may be identical or different, represent a linear or branched $C_1$ to $C_{30}$ alkylenediyl group, possibly containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, possibly comprising one or more oxygen, sulphur and/or nitrogen atoms, and/or bearing as substituent one of the following atoms or groups of atoms:
   fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
T represents a linear or branched, saturated or unsaturated, $C_3$ to $C_{24}$ trivalent or tetravalent hydrocarbon-based group optionally substituted with a polyorganosiloxane chain, and possibly containing one or more atoms chosen from O, N and S, or T represents a trivalent atom chosen from N, P and Al, and
$R^5$ represents a linear or branched $C_1$ to $C_{50}$ alkyl group or a polyorganosiloxane chain, possibly comprising one or more ester, amide, urethane, thiocarbamate, urea, urethane, thiourea and/or sulphonamide groups, which may be linked to another chain of the polymer;
5) the groups G, which may be identical or different, represent divalent groups chosen from:

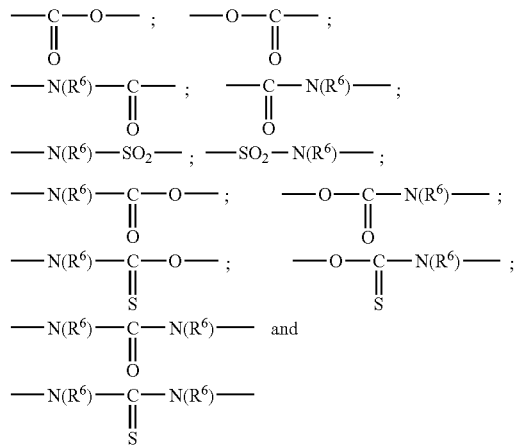

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

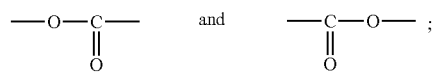

6) n is an integer ranging from 2 to 500 and preferably from 2 to 200, and m is an integer ranging from 1 to 1000, preferably from 1 to 700 and better still from 6 to 200.

According to the invention, 80% of the groups $R^1$, $R^2$, $R^3$ and $R^4$ of the polymer are preferably chosen from methyl, ethyl, phenyl and 3,3,3-trifluoropropyl groups.

According to the invention, Y can represent various divalent groups, furthermore optionally comprising one or two free valencies to establish bonds with other moieties of the polymer or copolymer. Preferably, Y represents a group chosen from:

a) linear $C_1$ to $C_{20}$ and preferably $C_1$ to $C_{10}$ alkylene groups, b) $C_{30}$ to $C_{56}$ branched alkylene groups possibly comprising rings and unconjugated unsaturations, c) $C_5$-$C_6$ cycloalkylene groups, d) phenylene groups optionally substituted with one or more $C_1$ to $C_{40}$ alkyl groups, e) $C_1$ to $C_{20}$ alkylene groups comprising from 1 to 5 amide groups, f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups, g) polyorganosiloxane chains of formula:

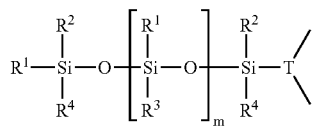

in which $R^1$, $R^2$, $R^3$, $R^4$, T and m are as defined above, and h) polyorganosiloxane chains of formula:

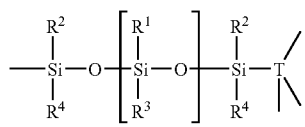

in which $R^1$, $R^2$, $R^3$, $R^4$, T and m are as defined above.

The polyorganosiloxanes of the second family may be polymers comprising at least one moiety corresponding to formula (II):

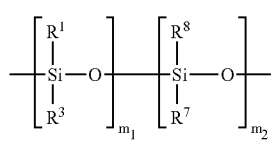
(II)

in which $R^1$ and $R^3$, which may be identical or different, are as defined above for formula (I), $R^7$ represents a group as defined above for $R^1$ and $R^3$, or represents a group of formula -X-G-$R^9$ in which X and G are as defined above for formula (I) and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula -X-G-$R^9$ in which X, G and $R^9$ are as defined above, $m_1$ is an integer ranging from 1 to 998, and $m_2$ is an integer ranging from 2 to 500.

According to the invention, the polymer used as structuring agent may be a homopolymer, that is to say a polymer comprising several identical moieties, in particular moieties of formula (I) or of formula (II).

According to the invention, it is also possible to use a copolymer comprising several different moieties of formula (I), that is to say a polymer in which at least one of the groups $R^1$, $R^2$, $R^3$, $R^4$, X, G, Y, m and n is different in one of the moieties. The copolymer may also be formed from several moieties of formula (II), in which at least one of the groups $R^1$, $R^3$, $R^7$, $R^8$, $m_1$ and $m_2$ is different in at least one of the moieties.

It is also possible to use a copolymer comprising at least one moiety of formula (I) and at least one moiety of formula (II), the moieties of formula (I) and the moieties of formula (II) possibly being identical to or different from each other.

According to one variant of the invention, it is also possible to use a copolymer furthermore comprising at least one hydrocarbon-based moiety comprising two groups capable of establishing hydrogen interactions, chosen from ester, amide, sulphonamide, carbamate, thiocarbamate, urea, urethane, thiourea oxamido, guanamido and biguanidino groups, and combinations thereof.

These copolymers may be block copolymers or grafted copolymers.

According to a first embodiment of the invention, groups capable of establishing hydrogen interactions are amide groups of formulae —C(O)NH— and —HN—C(O)—.

In this case, the structuring agent may be a polymer comprising at least one moiety of formula (III) or (IV):

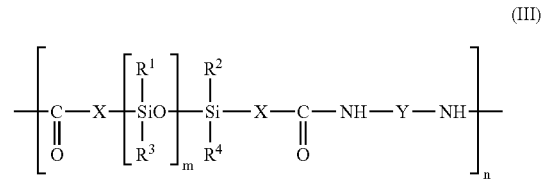
(III)

or

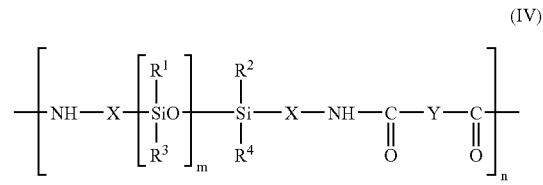
(IV)

in which $R^1$, $R^2$, $R^3$, $R^4$, X, Y, m and n are as defined above.

Such a moiety may be obtained:

either by a condensation reaction between a silicone containing α,ω-carboxylic acid ends and one or more diamines, according to the following reaction scheme:

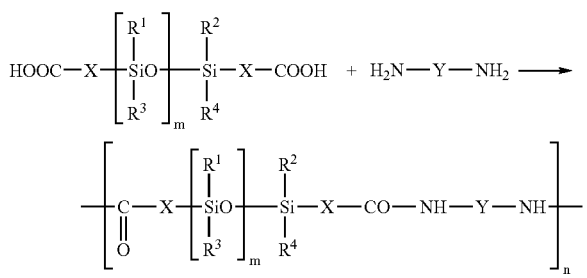

or by reaction of two molecules of α-unsaturated carboxylic acid with a diamine according to the following reaction scheme:

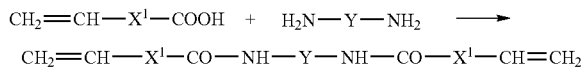

followed by the addition of a siloxane to the ethylenic unsaturations, according to the following scheme:

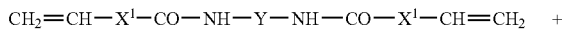

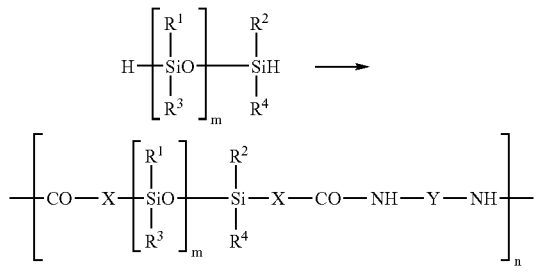

in which $X^1$—$(CH_2)_2$— corresponds to X defined above and Y, $R^1$, $R^2$, $R^3$, $R^4$ and m are as defined above;

or by reaction of a silicone containing α,ω-$NH_2$ ends and a diacid of formula HOOC—Y—COOH according to the following reaction scheme:

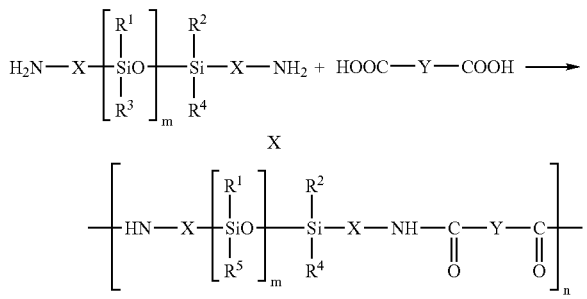

In these polyamides of formula (III) or (IV), m is preferably in the range from 1 to 700, more preferably from 15 to 500 and better still from 15 to 45, and n is in particular in the range from 1 to 500, preferably from 1 to 100 and better still from 4 to 25, X is preferably a linear or branched alkylene chain containing from 1 to 30 carbon atoms and in particular 3 to 10 carbon atoms, and Y is preferably an alkylene chain that is linear or branched or that possibly comprises rings and/or unsaturations, containing from 1 to 40 carbon atoms, in particular from 1 to 20 carbon atoms and better still from 2 to 6 carbon atoms, in particular 6 carbon atoms.

In formulae (III) and (IV), the alkylene group representing X or Y can optionally contain in its alkylene portion at least one of the following elements:

1°) 1 to 5 amide, urea or carbamate groups,

2°) a $C_5$ or $C_6$ cycloalkyl group, and

3°) a phenylene group optionally substituted with 1 to 3 identical or different $C_1$ to $C_3$ alkyl groups.

In formulae (III) and (IV), the alkylene groups may also be substituted with at least one element chosen from the group consisting of:

a hydroxyl group, a $C_3$ to $C_8$ cycloalkyl group, one to three $C_1$ to $C_{40}$ alkyl groups, a phenyl group optionally substituted with one to three $C_1$ to $C_3$ alkyl groups, a $C_1$ to $C_3$ hydroxyalkyl group, and a $C_1$ to $C_6$ aminoalkyl group.

In these formulae (III) and (IV), Y may also represent:

in which $R^5$ represents a polyorganosiloxane chain and T represents a group of formula:

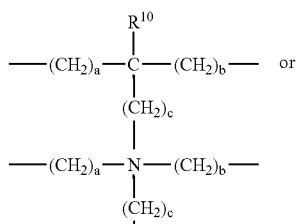

in which a, b and c are, independently, integers ranging from 1 to 10, and $R^{10}$ is a hydrogen atom or a group such as those defined for $R^1$, $R^2$, $R^3$ and $R^4$.

In formulae (III) and (IV), $R^1$, $R^2$, $R^3$ and $R^4$ preferably represent, independently, a linear or branched $C_1$ to $C_{40}$ alkyl group, preferably a $CH_3$, $C_2H_5$, n-$C_3H_7$ or isopropyl group, a polyorganosiloxane chain or a phenyl group optionally substituted with one to three methyl or ethyl groups.

As has been seen previously, the polymer may comprise identical or different moieties of formula (III) or (IV).

Thus, the polymer may be a polyamide containing several moieties of formula (III) or (IV) of different lengths, i.e. a polyamide corresponding to the formula:

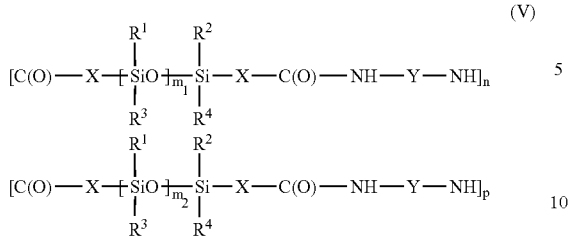

(V)

in which X, Y, n and $R^1$ to $R^4$ have the meanings given above, $m_1$ and $m_2$, which are different, are chosen in the range from 1 to 1 000, and p is an integer ranging from 2 to 300.

In this formula, the moieties may be structured to form either a block copolymer, or a random copolymer or an alternating copolymer. In this copolymer, the moieties may be not only of different lengths, but also of different chemical structures, for example containing different groups Y. In this case, the copolymer may correspond to the formula:

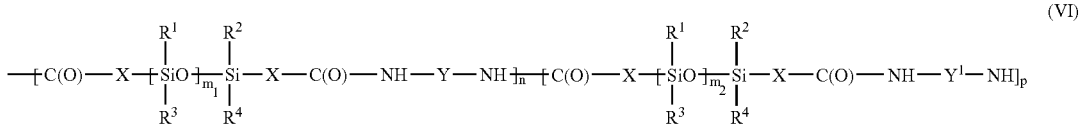

(VI)

in which $R^1$ to $R^4$, X, Y, $m_1$, $m_2$, n and p have the meanings given above and $Y^1$ is different from Y but chosen from the groups defined for Y. As previously, the various moieties may be structured to form either a block copolymer, or a random copolymer or an alternating copolymer.

In this first embodiment of the invention, the structuring polymer may also consist of a grafted copolymer. Thus, the polyamide containing silicone units may be grafted and optionally crosslinked with silicone chains containing amide groups. Such polymers may be synthesized with trifunctional amines.

In this case, the copolymer may comprise at least one moiety of formula:

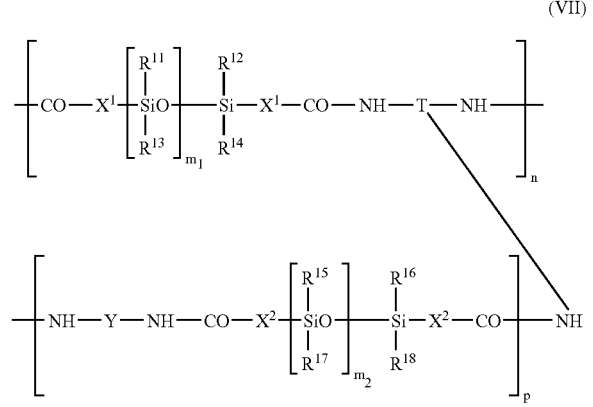

(VII)

in which $X^1$ and $X^2$, which may be identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1 000, and p is an integer ranging from 2 to 500.

In formula (VII), it is preferred that:

p is in the range from 1 to 25 and better still from 1 to 7, $R^{11}$ to $R^{18}$ are methyl groups, T corresponds to one of the following formulae:

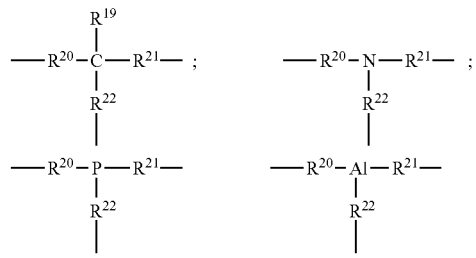

in which $R^{19}$ is a hydrogen atom or a group chosen from the groups defined for $R^1$ to $R^4$, and $R^{20}$, $R^{21}$ and $R^{22}$ are, independently, linear or branched alkylene groups, and more preferably corresponds to the formula:

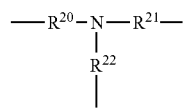

in particular with $R^{20}$, $R^{21}$ and $R^{22}$ representing —$CH_2$—$CH_2$—, $m_1$ and $m_2$ are in the range from 15 to 500 and better still from 15 to 45, $X^1$ and $X^2$ represent —$(CH_2)_{10}$—, and Y represents —$CH_2$—.

These polyamides containing a grafted silicone moiety of formula (VII) may be copolymerized with polyamide-silicones of formula (II) to form block copolymers, alternating copolymers or random copolymers. The weight percentage of grafted silicone moieties (VII) in the copolymer may range from 0.5% to 30% by weight.

According to the invention, the siloxane units may be in the main chain or backbone of the polymer, but they may also be present in grafted or pendent chains. In the main chain, the siloxane units may be in the form of segments as described above. In the pendent or grafted chains, the siloxane units may appear individually or in segments.

According to the invention, the preferred siloxane-based polyamides are:

polyamides of formula (III) in which m is from 15 to 50;

mixtures of two or more polyamides in which at least one polyamide has a value of m in the range from 15 to 50 and at least one polyamide has a value of m in the range from 30 to 50;

polymers of formula (V) with $m_1$ chosen in the range from 15 to 50 and $m_2$ chosen in the range from 30 to 500 with the portion corresponding to $m_1$ representing 1% to 99% by weight of the total weight of the polyamide and the corresponding portion $m_2$ representing 1% to 99% by weight of the total weight of the polyamide;

mixtures of polyamide of formula (III) combining 1) 80% to 99% by weight of a polyamide in which n is equal to 2 to 10 and in particular 3 to 6, and 2) 1% to 20% of a polyamide in which n is in the range from 5 to 500 and in particular from 6 to 100;

polyamides corresponding to formula (VI) in which at least one of the groups Y and $Y^1$ contains at least one hydroxyl substituent;

polyamides of formula (III) synthesized with at least one portion of an activated diacid (diacid chloride, dianhydride or diester) instead of the diacid;

polyamides of formula (III) in which X represents —$(CH_2)_3$— or —$(CH_2)_{10}$; and polyamides of formula (III) in which the polyamides end with a monofunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

According to the invention, the end groups of the polymer chain may end with:

a $C_1$ to $C_{50}$ alkyl ester group by introducing a $C_1$ to $C_{50}$ monoalcohol during the synthesis, a $C_1$ to $C_{50}$ alkylamide group by taking as stopping group a monoacid if the silicone is α,ω-diaminated, or a monoamine if the silicone is an α,ω-dicarboxylic acid.

According to one embodiment variant of the invention, it is possible to use a copolymer of silicone polyamide and of hydrocarbon-based polyamide, i.e. a copolymer comprising moieties of formula (III) or (IV) and hydrocarbon-based polyamide moieties. In this case, the polyamide-silicone moieties may be arranged at the ends of the hydrocarbon-based polyamide.

Polyamide-based structuring agents containing silicones may be produced by silylic amidation of polyamides based on fatty acid dimer. This approach involves the reaction of free acid sites existing on a polyamide as end sites, with organosiloxane-monoamines and/or organosiloxane-diamines (amidation reaction), or alternatively with oligosiloxane alcohols or oligosiloxane diols (esterification reaction). The esterification reaction requires the presence of acid catalysts, as is known in the art. It is desirable for the polyamide containing free acid sites, used for the amidation or esterification reaction, to have a relatively high number of acid end groups (for example polyamides with high acid numbers, for example from 15 to 20).

For the amidation of the free acid sites of the hydrocarbon-based polyamides, siloxane diamines with 1 to 300, more particularly 2 to 50 and better still 2, 6, 9.5, 12, 13.5, 23 or 31 siloxane groups, may be used for the reaction with hydrocarbon-based polyamides based on fatty acid dimers. Siloxane diamines containing 13.5 siloxane groups are preferred, and the best results are obtained with the siloxane diamine containing 13.5 siloxane groups and polyamides containing high numbers of carboxylic acid end groups.

The reactions may be carried out in xylene to extract the water produced from the solution by azeotropic distillation, or at higher temperatures (about 180 to 200° C.) without solvent. Typically, the efficacy of the amidation and the reaction rates decrease when the siloxane diamine is longer, that is to say when the number of siloxane groups is higher. Free amine sites may be blocked after the initial amidation reaction of the diaminosiloxanes by reacting them either with a siloxane acid, or with an organic acid such as benzoic acid.

For the esterification of the free acid sites on the polyamides, this may be performed in boiling xylene with about 1% by weight, relative to the total weight of the reagents, of para-toluenesulphonic acid as catalyst.

These reactions carried out on the carboxylic acid end groups of the polyamide lead to the incorporation of silicone moieties only at the ends of the polymer chain.

It is also possible to prepare a copolymer of polyamide-silicone, using a polyamide containing free amine groups, by amidation reaction with a siloxane containing an acid group.

It is also possible to prepare a structuring polymer based on a copolymer between a hydrocarbon-based polyamide and a silicone polyamide, by transamidation of a polyamide having, for example, an ethylene-diamine constituent, with an oligosiloxane-α,ω-diamine, at high temperature (for example 200 to 300° C.), to carry out a transamidation such that the ethylenediamine component of the original polyamide is replaced with the oligosiloxane diamine.

The copolymer of hydrocarbon-based polyamide and of polyamide-silicone may also be a grafted copolymer comprising a hydrocarbon-based polyamide backbone with pendent oligosiloxane groups.

This may be obtained, for example:

by hydrosilylation of unsaturated bonds in polyamides based on fatty acid dimers;

by silylation of the amide groups of a polyamide; or by silylation of unsaturated polyamides by means of an oxidation, that is to say by oxidizing the unsaturated groups into alcohols or diols, to form hydroxyl groups that are reacted with siloxane carboxylic acids or siloxane alcohols. The olefinic sites of the unsaturated polyamides may also be epoxidized and the epoxy groups may then be reacted with siloxane amines or siloxane alcohols.

According to a second embodiment of the invention, the structuring polymer consists of a homopolymer or a copolymer comprising urethane or urea groups.

As previously, the polymer may comprise polyorganosiloxane moieties containing two or more urethane and/or urea groups, either in the backbone of the polymer or on side chains or as pendent groups.

The polymers comprising at least two urethane and/or urea groups in the backbone may be polymers comprising at least one moiety corresponding to the following formula:

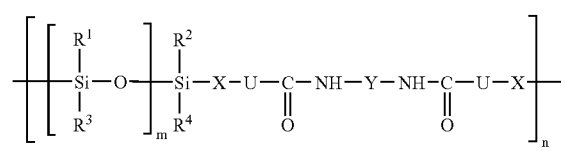

(VIII)

in which $R^1$, $R^2$, $R^3$, $R^4$, X, Y, m and n have the meanings given above for formula (I), and U represents —O— or —NH—, such that:

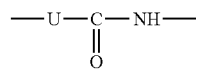

corresponds to a urethane or urea group.

In this formula (VIII), Y may be a linear or branched $C_1$ to $C_{40}$ alkylene group, optionally substituted with a $C_1$ to $C_{15}$ alkyl group or a $C_5$ to $C_{10}$ aryl group. Preferably, a —$(CH_2)_6$— group is used.

Y may also represent a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4'-biphenylenemethane. Generally, it is preferred for Y to represent a linear or branched $C_1$ to $C_{40}$ alkylene radical or a $C_4$ to $C_{12}$ cycloalkylene radical.

Y may also represent a polyurethane or polyurea block corresponding to the condensation of several diisocyanate molecules with one or more molecules of coupling agents of the diol or diamine type. In this case, Y comprises several urethane or urea groups in the alkylene chain.

It may correspond to the formula:

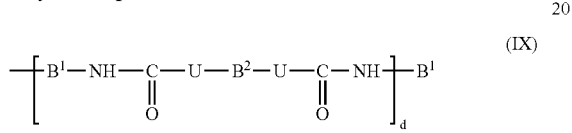

(IX)

in which $B^1$ is a group chosen from the groups given above for Y, U is —O— or —NH— and $B^2$ is chosen from:
- linear or branched $C_1$ to $C_{40}$ alkylene groups, which can optionally bear an ionizable group such as a carboxylic acid or sulphonic acid group, or a neutralizable or quaternizable tertiary amine group,
- $C_5$ to $C_{12}$ cycloalkylene groups, optionally bearing alkyl substituents, for example one to three methyl or ethyl groups, or alkylene, for example the diol radical: cyclohexanedimethanol,
- phenylene groups that may optionally bear $C_1$ to $C_3$ alkyl substituents, and
- groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

T can represent, for example:

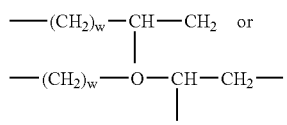

with w being an integer ranging from 1 to 10 and $R^5$ being a polyorganosiloxane chain.

When Y is a linear or branched $C_1$ to $C_{40}$ alkylene group, the —$(CH_2)_2$— and —$(CH_2)_6$— groups are preferred.

In the formula given above for Y, d may be an integer ranging from 0 to 5, preferably, from 0 to 3 and more preferably equal to 1 or 2.

Preferably, $B^2$ is a linear or branched $C_1$ to $C_{40}$ alkylene group, in particular —$(CH_2)_2$— or —$(CH_2)_6$— or a group:

with $R^5$ being a polyorganosiloxane chain.

As previously, the structuring polymer may be formed from silicone urethane and/or silicone urea moieties of different length and/or constitution, and may be in the form of block or random copolymers.

According to the invention, the silicone may also comprise urethane and/or urea groups no longer in the backbone but as side branches.

In this case, the polymer may comprise at least one moiety of formula:

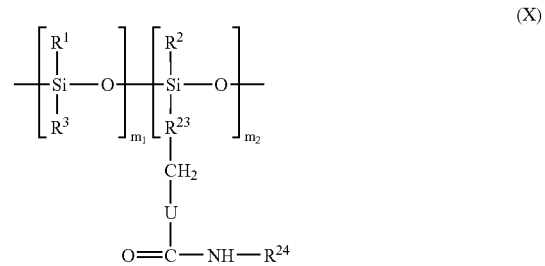

(X)

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

The polymers comprising at least one moiety of formula (X) contain siloxane units and urea or urethane groups, and they may be used as structuring agents in the compositions of the invention.

The siloxane polymers may have a single urea or urethane group by branching or may have branches containing two urea or urethane groups, or alternatively they may contain a mixture of branches containing one urea or urethane group and branches containing two urea or urethane groups.

They may be obtained from branched polysiloxanes, comprising one or two amino groups by branching, by reacting these polysiloxanes with monoisocyanates.

As examples of starting polymers of this type containing amino and diamino branches, mention may be made of the polymers corresponding to the following formulae:

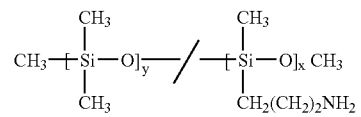

y = 57; x = 3

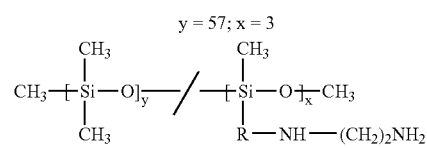

y = 56; x = 4

In these formulae, the symbol "/" indicates that the segments may be of different lengths and in a random order, and R represents a linear aliphatic group preferably containing 1 to 6 carbon atoms and better still 1 to 3 carbon atoms.

Such polymers containing branching may be formed by reacting a siloxane polymer, containing at least three amino groups per polymer molecule, with a compound containing only one monofunctional group (for example an acid, an isocyanate or an isothiocyanate) to react this monofunctional group with one of the amino groups and to form groups capable of establishing hydrogen interactions. The amino groups may be on side chains extending from the main chain of the siloxane polymer, such that the groups capable of establishing hydrogen interactions are formed on these side chains, or alternatively the amino groups may be at the ends of the main chain, such that the groups capable of hydrogen interaction will be end groups of the polymer.

As a procedure for forming a polymer containing siloxane units and groups capable of establishing hydrogen interactions, mention may be made of the reaction of a siloxane diamine and of a diisocyanate in a silicone solvent so as to provide a gel directly. The reaction may be performed in a silicone fluid, the resulting product being dissolved in the silicone fluid, at high temperature, the temperature of the system then being reduced to form the gel.

The polymers that are preferred for incorporation into the compositions according to the present invention are siloxane-urea copolymers that are linear and that contain urea groups as groups capable of establishing hydrogen interactions in the backbone of the polymer.

As an illustration of a polysiloxane ending with four urea groups, mention may be made of the polymer of formula:

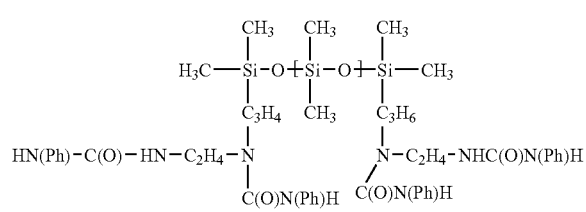

(XI)

(Ph = Phenyl)

in which Ph is a phenyl group and n is a number from 0 to 300, in particular from 0 to 100, for example 50.

This polymer is obtained by reacting the following polysiloxane containing amino groups:

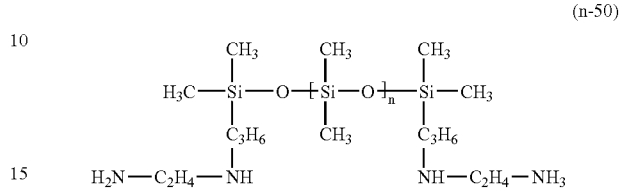

(n-50)

with phenyl isocyanate.

The polymers of formula (VIII) comprising urea or urethane groups in the chain of the silicone polymer may be obtained by reaction between a silicone containing $\alpha,\omega$-$NH_2$ or —OH end groups, of formula:

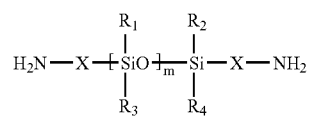

in which m, $R^1$, $R^2$, $R^3$, $R^4$ and X are as defined for formula (I) and a diisocyanate OCN—Y—NCO in which Y has the meaning given in formula (I); and optionally a diol or diamine coupling agent of formula $H_2N$—$B^2$—$NH_2$ or HO—$B^2$—OH, in which $B^2$ is as defined in formula (IX).

According to the stoichiometric proportions between the two reagents, diisocyanate and coupling agent, Y may have the formula (IX) with d equal to 0 or d equal to 1 to 5.

As in the case of the polyamide silicones of formula (II) or (III), it is possible to use in the invention polyurethane or polyurea silicones containing moieties of different length and structure, in particular moieties whose lengths differ by the number of silicone units. In this case, the copolymer may correspond, for example, to the formula:

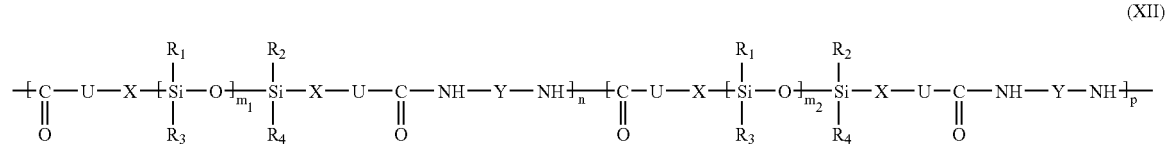

(XII)

in which $R^1$, $R^2$, $R^3$, $R^4$, X, Y and U are as defined for formula (VIII) and $m_1$, $m_2$, n and p are as defined for formula (V).

Branched polyurethane or polyurea silicones may also be obtained using, instead of the diisocyanate OCN—Y—NCO, a triisocyanate of formula:

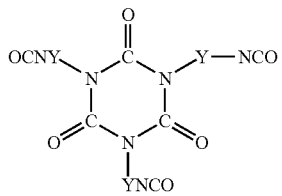

A polyurethane or polyurea silicone containing branches comprising an organosiloxane chain with groups capable of establishing hydrogen interactions is thus obtained. Such a polymer comprises, for example, a moiety corresponding to the formula:

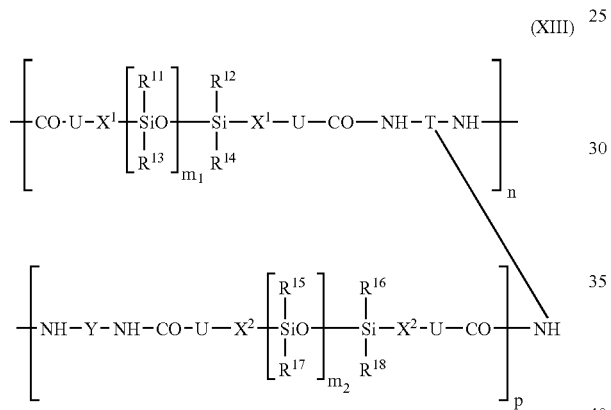

(XIII)

in which $X^1$ and $X^2$, which are identical or different, have the meaning given for X in formula (I), n is as defined in formula (I), Y and T are as defined in formula (I), $R^{11}$ to $R^{18}$ are groups chosen from the same group as $R^1$ to $R^4$, $m_1$ and $m_2$ are numbers in the range from 1 to 1 000, and p is an integer ranging from 2 to 500.

As in the case of the polyamides, this copolymer can also comprise polyurethane silicone moieties without branching.

In this second embodiment of the invention, the siloxane-based polyureas and polyurethanes that are preferred are:
polymers of formula (VIII) in which m is from 15 to 50;
mixtures of two or more polymers in which at least one polymer has a value of m in the range from 15 to 50 and at least one polymer has a value of m in the range from 30 to 50;
polymers of formula (XII) with $m_1$ chosen in the range from 15 to 50 and $m_2$ chosen in the range from 30 to 500 with the portion corresponding to $m_1$ representing 1% to 99% by weight of the total weight of the polymer and the portion corresponding to $m_2$ representing 1% to 99% by weight of the total weight of the polymer;
mixtures of polymer of formula (VIII) combining
1) 80% to 99% by weight of a polymer in which n is equal to 2 to 10 and in particular 3 to 6, and
2) 1% to 20% of a polymer in which n is in the range from 5 to 500 and in particular from 6 to 100,
copolymers comprising two moieties of formula (VIII) in which at least one of the groups Y contains at least one hydroxyl substituent;
polymers of formula (VIII) synthesized with at least one portion of an activated diacid (diacid chloride, dianhydride or diester) instead of the diacid;
polymers of formula (VIII) in which X represents —$(CH_2)_3$— or —$(CH_2)_{10}$—; and
polymers of formula (VIII) in which the polymers end with a multifunctional chain chosen from the group consisting of monofunctional amines, monofunctional acids, monofunctional alcohols, including fatty acids, fatty alcohols and fatty amines, such as, for example, octylamine, octanol, stearic acid and stearyl alcohol.

As in the case of the polyamides, copolymers of polyurethane or polyurea silicone and of hydrocarbon-based polyurethane or polyurea may be used in the invention by performing the reaction for synthesizing the polymer in the presence of an α,ω-difunctional block of non-silicone nature, for example a polyester, a polyether or a polyolefin.

As has been seen previously, the structuring polymer of the invention may contain siloxane moieties in the main chain of the polymer and groups capable of establishing hydrogen interactions, either in the main chain of the polymer or at the ends thereof, or on side chains or branches of the main chain. This may correspond to the following five arrangements:

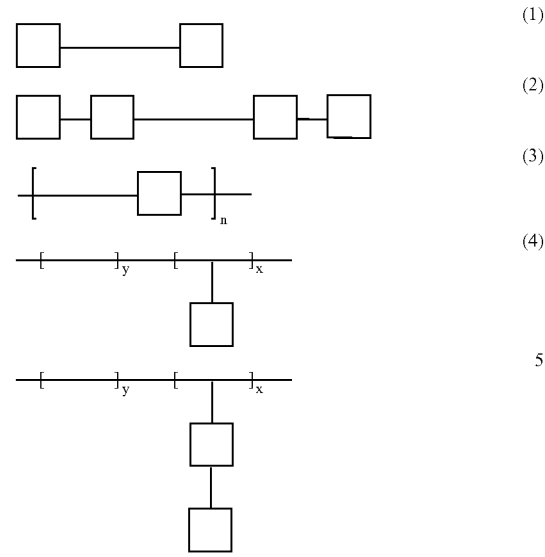

in which the continuous line is the main chain of the siloxane polymer and the squares represent the groups capable of establishing hydrogen interactions.

In case (1), the groups capable of establishing hydrogen interactions are arranged at the ends of the main chain.

In case (2), two groups capable of establishing hydrogen interactions are arranged at each of the ends of the main chain.

In case (3), the groups capable of establishing hydrogen interactions are arranged within the main chain in repeating moieties.

In cases (4) and (5), these are copolymers in which the groups capable of establishing hydrogen interactions are arranged on branches of the main chain of a first series of moieties that are copolymerized with moieties not comprising groups capable of establishing hydrogen interactions. The values n, x and y are such that the polymer has the desired properties in terms of an agent for gelling fatty phases based on silicone oil.

According to the invention, the structuring of the liquid fatty phase can be obtained with the aid of one or more of the polymers mentioned above. As examples of polymers that may be used, mention may be made of the silicone polyamides obtained in accordance with Examples 1 and 2 of document U.S. Pat. No. 5,981,680.

The at least one structuring polymer in the compositions of the invention may have a softening point greater than 50° C., such as from 65° C. to 190° C., and for example less than 150° C., and further such as from 70° C. to 130° C., and even further such as from 80° C. to 105° C. This softening point may be lower than that of structuring polymers used in the art which may facilitate the use of the at least one structuring polymer of the present invention and may limit the degradation of the liquid fatty phase. These polymers may be non waxy polymers.

The softening point can be measured by a well known method as "Differential Scanning Calorimetry" (i.e. DSC method) with a temperature rise of 5 to 20° C./min.

The at least one structuring polymer has good solubility in the silicone oils and produces macroscopically homogeneous compositions. Preferably, they have an average molecular weight from 500 to 300,000, for example from 1,000 to 160,000 and preferably from 40,000 to 120,000.

Preferable structuring polymers useful herein are solids that may be dissolved beforehand in a solvent with hydrogen interaction capable of breaking the hydrogen interactions of the polymers, for instance $C_2$ to $C_8$ lower alcohols and especially ethanol, n-propanol or isopropanol, before being placed in the presence of the silicone oils according to the invention. It is also possible to use these hydrogen interaction "breaking" solvents as co-solvents. These solvents may then be stored in the composition or may be removed by selective evaporation, which is well known to those skilled in the art.

Oil

The invention compositions comprise at least one oil. The compositions of the invention described as comprising a liquid fatty phase comprise this at least one oil at least partially in this phase. The expression "liquid fatty phase" means a fatty phase which is liquid at room temperature (25° C.) and atmospheric pressure (760 mmHg, i.e. 101 kPa), composed of one or more oils that are liquid at room temperature, that are generally mutually compatible, i.e. forming a homogeneous phase macroscopically. Preferably, the oil is present is an amount of 0.01-99%, more preferably 1-75%, even more preferably 2-50%, 10-80%, 20-80%, 35-65%, etc., including of course 1-35% (and further including all values in each range stated) by weight with respect to the total weight of the composition.

The at least one oil may preferably be chosen from hydrocarbon-based liquid oils (i.e., hydrocarbons, alkanes) and silicone oils such as dimethicones, for example DC200, SC 96, etc. Preferably the silicone oil, including the dimethicones, has a viscosity of up to 350 centistokes.

The liquid fatty phase of the composition, when present, may contain more than 30%, for example, more than 40%, of liquid oil(s). For the purposes of the invention, the expression "hydrocarbon-based oil" means an oil essentially comprising carbon and hydrogen atoms, optionally with at least one group chosen from hydroxyl, ester, carboxyl and ether groups.

For a liquid fatty phase structured with a polymer containing a partially silicone-based skeleton, this fatty phase may contain more than 30%, for example, more than 40%, relative to the total weight of the liquid fatty phase and, for example, from 50% to 100%, of at least one silicone-based liquid oil, relative to the total weight of the liquid fatty phase.

Useful silicone oils may be chosen from volatile and non-volatile, linear and cyclic polydimethylsiloxanes (PDMSs) that are liquid at room temperature; polydimethylsiloxanes comprising alkyl or alkoxy groups which are pendant and/or at the end of the silicone chain, the groups each containing from 2 to 24 carbon atoms, phenylsilicones such as phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates. Hydrocarbon-based liquid oils include those chosen from linear and branched, volatile and non-volatile hydrocarbons of synthetic and mineral origin, such as volatile liquid paraffins (such as isoparaffins and isododecane) or non-volatile liquid paraffins and derivatives thereof, liquid petrolatum, liquid lanolin, polydecenes, hydrogenated polyisobutene such as Parleam®, and squalane; and mixtures thereof.

In practice, the total liquid fatty phase can be, for example, present in an amount ranging from 1% to 99% by weight relative to the total weight of the composition, for example from 5% to 99%, 5% to 95.5%, from 10% to 80% or from 20% to 75%.

For the purposes of the invention, the expression "volatile solvent or oil" means any non-aqueous medium capable of evaporating on contact with the skin or the lips in less than one hour at room temperature and atmospheric pressure. The volatile solvent(s) of the invention is(are) organic solvents, such as volatile cosmetic oils that are liquid at room temperature, having a non-zero vapor pressure, at room temperature and atmospheric pressure, ranging in particular from $10^{-2}$ to 300 mmHg (1.33 to 40 000 Pa) and, for example, greater than 0.03 mmHg (4 Pa) and further example greater than 0.3 mmHg (40 Pa). The expression "non-volatile oil" means an oil which remains on the skin or the lips at room temperature and atmospheric pressure for at least several hours, such as those having a vapor pressure of less than $10^{-2}$ mmHg (1.33 Pa).

According to the invention, these volatile solvents may facilitate the staying power or long wearing properties of the composition on the skin, the lips or superficial body growths such as nails and keratinous fibers. The solvents can be chosen from hydrocarbon-based solvents, silicone solvents optionally comprising alkyl or alkoxy groups that are pendant or at the end of a silicone chain, and a mixture of these solvents.

The volatile oil(s), in one embodiment, can be present in an amount ranging from 0% to 95.5% relative to the total weight of the composition, such as from 2% to 75% or, for example, from 10% to 45%. This amount will be adapted by a person skilled in the art according to the desired staying power or long wearing properties.

Coated Silicone Elastomer

The invention composition comprises at least one coated silicone elastomer, also referred to as a hybrid silicone particle or powder. This coated silicone elastomer is constituted by a silicone rubber coated with silicone resin, where the resin structure is preferably bonded to the rubber structure. These materials may be further functionalized with, e.g., fluoroalkyl, phenyl, etc. groups. Preferred coated silicone elastomers used according to the invention are the KSP series of hybrid silicone powders (e.g., KSP 100, 101, 102, 103, 104, 105, 200 and 300) from Shin Etsu, the product brochures of which are incorporated herein by reference. Also useful herein are the materials described in U.S. Pat. No. 5,538,793, incorporated herein by reference, for example particles having a composite structure consisting of a spherical or globular particle of a cured silicone rubber having an average particle diameter in the range from 0.1 to 100 um and a coating layer of a polyorganosilsesquioxane resin, the coating amount of the polyorganosilsesquioxane resin being in the range from 1 to 500 parts by weight per 100 parts by weight of the silicone rubber particles without coating. Useful materials are also described in U.S. Pat. No. 6,376,078, incorporated herein by reference.

The coated silicone elastomer is preferably present in the invention compositions in an amount of from 0.01-99%, more likely 0.1-75%, preferably 1-50%, 0.5-25%, etc., all values between each range being specifically included as if written out, based on total weight of the composition. Preferably, the particle size of the coated silicone elastomer ranges from 2-30 um, and their hardness varies from 30-75 (Durometer Type A).

Additional Ingredients

The composition of the invention can also comprise any additive or ingredient used in the field under consideration, chosen for example from dispersants such as poly(2-hydroxystearic acid), antioxidants, essential oils, preserving agents, fragrances, waxes, liposoluble polymers that are dispersible in the medium, fillers, neutralizing agents, cosmetic and dermatological active agents such as, for example, emollients, moisturizers, vitamins, essential fatty acids, sunscreens, colorants and mixtures thereof. These additives may be present in the composition in a proportion of from 0% to 20% (such as from 0.01% to 20%) relative to the total weight of the composition and further such as from 0.01% to 10% (if present).

The composition of the invention can also contain, as an additive, an aqueous phase containing water that is optionally thickened or gelled with an aqueous-phase thickener or gelling agent and/or containing ingredients soluble in water. The water can represent from 0.01 to 50%, for example from 0.5 to 30% relative to the total weight of the composition. However, anhydrous compositions are preferred. Particularly preferred are anhydrous compositions in the form of creams and pastes.

For the purposes of the invention, useful waxes are those generally used in cosmetics and dermatology; they include, for example, waxes of natural origin, for instance beeswax, carnauba wax, candelilla wax, ouricury wax, Japan wax, cork fibre wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methylsiloxanes and/or poly(di)methyl-siloxane esters that are solid at 40° C., for example, at above 55° C. Preferred waxes that may be used in the invention compositions include polyethylene and silicone waxes, preferably having a number average molecular weight of approximately 400-1500, but higher and lower molecular weights can be used.

Additional ingredients which may be used in the composition include crystalline silicone compounds. A crystalline silicone compound is a compound comprising silicone in its molecule, which is solid at room temperature, and has a crystalline character. Particularly useful crystalline silicone compounds belong to a class of alkyl siloxane waxes corresponding to the formulae below:

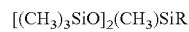

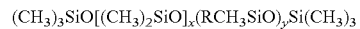

This could also be written as $R_3SiO[(CH_3)_2SiO]_x(RCH_3SiO)_ySiR_3$ where R is an alkyl chain. x may be 0-200 and y may be 0-200. The substituent R denotes an alkyl chain that may be as low as 1 or as high as 50 or more carbons as long as this silicone compound crystallizes at room temperature. Examples of crystalline silicone compounds include, but are not limited to, C20-24 Alkyl Methicone, C24-28 Alkyl Dimethicone, C20-24 Alkyl Dimethicone, C24-28 Alkyl Dimethicone commercially available from Archimica Fine Chemicals, Gainesville, Fla. under the designation of SilCare 41M40, SilCare 41M50, SilCare 41M70 and SilCare 41M80. Stearyl Dimethicone available as SilCare 41M65 from Archimica or as DC-2503 from Dow-Corning, Midland, Mich. Similarly, stearoxytrimethylsilane sold as SilCare 1M71 or DC-580 may be used in an embodiment of this invention. Furthermore, similar crystalline compounds are available from Degussa Care Specialties, Hopewell, Va. under the designation ABIL Wax 9810, 9800, or 2440, or Wacker-Chemie GmbH, Burghausen, Germany, under the designation BelSil SDM 5055, or OSi Specialties, Greenwich, Conn. under the designation Silsoft. Other crystalline silicone compounds include C30-45 Alkyl Methicone available from Dow Corning as AMS-C30 Wax, as well as GE's SF1642, or SF-1632 available from General Electric, Fairfield, Conn.

Needless to say, a person skilled in the art will take care to select the optional additional additives and/or the amount thereof such that the advantageous properties of the composition according to the invention are not, or are not substantially, adversely affected by the envisaged addition.

The composition according to the invention can be in any form including the form of a tinted or non tinted dermatological composition or a care composition for keratin materials such as the skin, the lips and/or superficial body growths, in the form of an antisun composition or body hygiene composition in particular in the form of a deodorant product or make-up-removing product in stick form. It can be used in particular as a care base for the skin, superficial body growths or the lips (lip balms, for protecting the lips against cold and/or sunlight and/or the wind, or care cream for the skin, the nails or the hair). As defined herein, a deodorant product is personal hygiene product and does not relate to care, make-up or treatment of keratin materials, including keratinous fibers.

The composition of the invention may also be in the form of a colored make-up product for the skin, in particular a foundation, optionally having care or treating properties, a blusher, a face powder, an eye shadow, a concealer product, an eyeliner, a make-up product for the body; a make-up product for the lips such as a lipstick, optionally having care or treating properties; a make-up product for superficial body growths such as the nails or the eyelashes, in particular in the form of a mascara cake, or for the eyebrows and the hair, in particular in the form of a pencil.

Needless to say, the composition of the invention should be cosmetically or dermatologically acceptable, i.e. it should contain a non-toxic physiologically acceptable medium and should be able to be applied to the skin, superficial body growths or the lips of human beings. For the purposes of the invention, the expression "cosmetically acceptable" means a composition of pleasant appearance, odor, feel and taste.

The composition advantageously contains at least one cosmetic active agent and/or at least one dermatological active agent, i.e., an agent having a beneficial effect on the skin, lips or body growths and/or at least one coloring agent.

Coloring Agents

The composition may further comprise at least one coloring agent (colorant). The coloring agent according to the invention may be chosen from the lipophilic dyes, hydrophilic dyes, pigments and nacreous pigments (i.e., nacres) usually used in cosmetic or dermatological compositions, and mixtures thereof. This coloring agent is generally present in a proportion of from 0.01% to 50% relative to the total weight of the composition, such as from 0.5% to 40% and further such as from 5% to 30%, if it is present. In the case of a composition in the form of a free or compacted powder, the amount of coloring agent in the form of solid particles that are insoluble in the medium (nacres and/or pigments) may be up to 90% relative to the total weight of the composition.

The liposoluble dyes are, for example, Sudan Red, D&C Red 17, D&C Green 6, β-carotene, soybean oil, Sudan Brown, D&C Yellow 11, D&C Violet 2, D&C Orange 5, quinoline yellow or annatto. They can represent from 0.1% to 20% of the weight of the composition, for example, from 0.1% to 6% (if present). The water-soluble dyes are, for example, beetroot juice or methylene blue, and can represent up to 6% of the total weight of the composition.

The pigments may be white or colored, goniochromatic or not, mineral and/or organic, and coated or uncoated. Among the mineral pigments which may be mentioned are titanium dioxide, optionally surface-treated, zirconium oxide, zinc oxide or cerium oxide, as well as iron oxide, chromium oxide, manganese violet, ultramarine blue, chromium hydrate and ferric blue. Among the organic pigments which may be mentioned are carbon black, pigments of D & C type, and lakes based on cochineal carmine or on barium, strontium, calcium or aluminum. The pigments can represent from 0.1% to 50%, such as from 0.5% to 40% and further such as from 2% to 30% relative to the total weight of the composition, if they are present.

The nacreous pigments may be chosen from white nacreous pigments such as mica coated with titanium or with bismuth oxychloride, colored nacreous pigments such as titanium mica with iron oxides, titanium mica with, in particular, ferric blue or chromium oxide, titanium mica with an organic pigment of the type mentioned above, as well as nacreous pigments based on bismuth oxychloride. They can represent, for example, from 0.1% to 20% relative to the total weight of the composition, and further such as from 0.1% to 15%, if they are present.

In one embodiment, the coloring agent is a pigment (nacreous or not).

The composition according to the invention may be manufactured by adapting known processes that are generally used in cosmetics or dermatology. It may be manufactured by a process which comprises mixing the necessary ingredients, optionally divided into phases. The mixture obtained can then be cast in a suitable mould such as a lipstick mould or directly into the packaging articles (case or dish in particular). Such processes are well within the ordinary skill of the artisan in view of this disclosure.

The hardness of the invention composition may also be considered. The hardness of a composition may, for example, be expressed in gramforce (gf). The composition of the present invention may, for example, have a hardness ranging from 20 gf to 2000 gf, such as from 20 gf to 900 gf, and further such as from 20 gf to 600 gf.

This hardness is measured in one of two ways. A first test for hardness is according to a method of penetrating a probe into the composition and in particular using a texture analyzer (for example TA-XT2 from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed. The measurement error is ±50 gf.

The second test for hardness is the "cheese wire" method, which involves cutting an 8.1 mm or preferably 12.7 mm in diameter stick composition and measuring its hardness at 20° C. using a DFGHS 2 tensile testing machine from Indelco-Chatillon Co. at a speed of 100 mm/minute. The hardness value from this method is expressed in grams as the shear force required to cut a stick under the above conditions. According to this method, the hardness of compositions according to the present invention which may be in stick form may, for example, range from 30 gf to 300 gf, such as from 30 gf to 250 gf, and further such as from 30 gf to 200 gf.

The hardness of the composition of the present invention may be such that the compositions are self-supporting and can easily disintegrate to form a satisfactory deposit on a keratinous material. In addition, this hardness may impart good impact strength to the inventive compositions which may be molded or cast, for example, in stick or dish form.

The skilled artisan may choose to evaluate a composition using at least one of the tests for hardness outlined above based on the application envisaged and the hardness desired. If one obtains an acceptable hardness value, in view of the intended application, from at least one of these hardness tests, the composition falls within the scope of the invention.

As is evident, the hardness of the composition according to the invention may, for example, be such that the composition is advantageously self-supporting and can disintegrate easily to form a satisfactory deposit on the skin and/or the lips and/or superficial body growths, such as keratinous fibers. In addition, with this hardness, the composition of the invention may have good impact strength.

According to the invention, the composition in stick form may have the behavior of a deformable, flexible elastic solid, giving noteworthy elastic softness on application. The compositions in stick form of the prior art do not have these properties of elasticity and flexibility.

EXAMPLES

Example 1

The following gelled makeup was prepared, where amounts are weight %:

| Ingredient name | Phase |
|---|---|
| 4.00 Polyethylene | |
| 10.00 Nylon-611/Dimethicone Copolymer DC 8179 | A |
| 10.00 Vinyl Dimethicone/Methicone silsesquioxane crosspolymer KSP-101 | |
| 50.00 Dimethicone DC200 @ 10 cst | |
| 5.00 Triisononanoin | |
| 9.48 Talc, Hydrogenated C12-18 Triglyceride, Methicone | B |
| 0.40 Red Iron oxide, Isopropyl titanium triisostearate | |
| 0.72 Iron Oxide yellow, Isopropyl titanium triisostearate | |
| 0.40 Ultramarine Blue, Isopropyl titanium triisostearate | |
| 3.00 TiO2 | |
| 4.00 Ultrafine TiO2 | |
| TiO2, Isopropyl titanium triisostearate | |
| Ultrafine TiO2, Isopropyl titanium triisostearate | |
| Silica | |
| 3.00 Silica | |
| 100.00 | |

-continued

| Ingredient name | Phase |
|---|---|
| 3 VP/hexadecene copolymer | |
| 24 D6 cyclomethicone | |
| 20 isododecane | |
| 9.48 Talc, hydrogenated C12-18 triglyceride, methicone | B |
| 0.4 red iron oxide, isopropyl titanium triisostearate | |
| 0.72 iron oxide yellow, isopropyl titanium triisostearate | |
| 0.4 Ultramarine blue, isopropyl titanium triisostearate | |
| 3 TiO2, isopropyl titanium triisostearate | |
| 4 ultrafine TiO2, isopropyl titanium triisostearate | |
| 3 silica | |
| 4 PMMA | |
| 4 mica | |
| 100 | |

Example 3

The following foundation makeup was prepared:

| Phase | Trade Name | INCI Name | % w/w |
|---|---|---|---|
| A1 | DC 245 Fluid | Cyclopentasiloxane | 15.00 |
| | DC 2-8179 | NYLON-611/DIMETHICONE COPOLYMER | 2.00 |
| | DC 200 Fluid 10 cst | Dimethicone | 4.00 |
| A2 | DOW CORNING 5225 C FORMULATION AID | CYCLOPENTASILOXANE (and) DIMETHICONE COPOLYOL | 8.00 |
| | Abil WE 09 | POLYGLYCERYL-4 ISOSTEARATE (and) HEXYL LAURATE (and) CETYL PEG/PPG-10/1 DIMETHICONE | 3.50 |
| | ITT-Titanium Dioxide | ITT-Titanium Dioxide | 8.45 |
| | ITT-Iron Oxide - Yellow | ITT-Iron Oxides | 1.00 |
| | ITT-Iron Oxide - Red | ITT-Iron Oxides (and) Iron Oxides | 0.42 |
| | ITT-Iron Oxide - Black | ITT-Iron Oxides (and) Iron Oxides | 0.13 |
| B1 | KSP-100 | VINYL DIMETHICONE/METHICONE SILSESQUIOXANE CROSSPOLYMER | 3.00 |
| | DC 200 Fluid 10 cst | Dimethicone | 6.00 |
| | GANZPEARL GMX-0610 | MMA Crosspolymer | 3.00 |
| | ORGASOL 2002 | Nylon-12 | 1.00 |
| B2 | Propylparaben | Propylparaben | 0.40 |
| | Bentone 38V | Disteardimonium Hectorite | 0.60 |
| | Propylene Carbonate | Propylene Carbonate | 0.30 |
| C | Water | Water | 41.00 |
| | Magnesium Sulfate | Magnesium Sulfate | 1.00 |
| | Methylparaben | Methylparaben | 0.20 |
| | BRIJ 30 | Laureth-4 | 0.50 |
| | Phenoxyethanol | Phenoxyethanol | 0.50 |
| | | Total: | 100.00 |

Example 2

The following gelled makeup was prepared, where amounts are weight %:

| Ingredient name | Phase |
|---|---|
| 1 Dimethicone copolyol beeswax | A |
| 9 Nylon-611/Dimethicone Copolymer DC 8179 | |
| 5 Vinyl Dimethicone/Methicone silsesquioxane crosspolymer KSP-100 | |
| 5 Dimethicone (DC200@10 cst) | |
| 4 C12-15 alkyl benzoate | |

Other materials useful herein, particularly elastomer particles, are described in: Tokkai2000-038314, Tokkai2000-038316, Tokkai2000-038317, Tokkai2000-038321, Tokkaihei9-020631, Tokkaihei10-120903, Tokkaihei11-335228, Tokkaihei 11-335242, Tokkaihei11-335254, Tokkai2000-086429, Tokkai2000-086427, Tokkai2000-086438, U.S. Pat. No. 5,538,793, WO02092047, WO0203951, WO0203950, WO0203935, WO0203932, EP0958804, EP0958085, EP1062944, EP1062959, EP1213011, EP1213316, EP1095959, U.S. Pat. Nos. 6,479,686, 6,475,500, US2002/0131947, US2002/0159964, US2001/0014312, US2002/0114771, U.S. Pat. No. 6,399,081, US2002/0058053, US2002/0081323, US2002/0102225, US2002/0114771, US2002/0131947 and US2002/0141958, all incorporated herein by reference.

The disclosures of U.S. application Ser. Nos. 10/166,760, 10/166,755, 10/320,599, 10/320,601, and 10/320,600 are incorporated herein by reference, as are all references, texts, articles, documents, product information, tests, standards, patents, applications, etc referred to above. Where ranges or limits are mentioned the endpoints are included, as usual, as are all values and subranges therewithin as if specifically written out.

The invention claimed is:

1. A composition comprising:
   (i) at least one structuring polymer having a weight-average molecular weight of from 500 to 500,000 and comprising at least one moiety comprising:
      at least one polyorganosiloxane group, comprising from 1 to 1,000 organosiloxane units in the chain of the moiety or in the form of a graft, and
      at least two groups, which may be the same or different, selected from the group consisting of ester, amide, sulphonamide, carbamate, thiocarbamate, urea, urethane, thiourea, oxamido, guanamido and biguanidino groups
      the structuring polymer being solid at 25° C.;
   (ii) at least one oil selected from the group consisting of hydrocarbon-based liquid oils and silicone oils; and
   (iii) silicone elastomer particles comprising a composite of spherical or globular particles of cured silicone rubber having an average particle size of from 0.1 to 100 μm and a coating layer of a polyorganosilsesquioxane resin bonded to the spherical or globular particles of cured silicone rubber, wherein the coating is present in an amount of from 1 to 500 parts by weight per 100 parts by weight of the particles of cured silicone rubber.

2. Composition according to claim 1, in which the structuring polymer comprises at least one moiety corresponding to the formula (I):

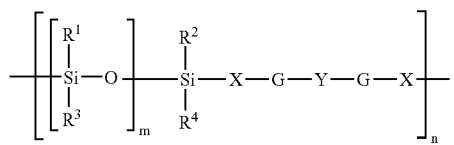

in which:
1) $R^1$, $R^2$, $R^3$ and $R^4$, which may be identical or different, represent a group chosen from:
   linear, branched or cyclic, saturated or unsaturated, $C_1$ to $C_{40}$ hydrocarbon-based groups, possibly containing in their chain one or more oxygen, sulphur and/or nitrogen atoms, and optionally being partially or totally substituted with fluorine atoms,
   $C_6$ to $C_{10}$ aryl groups, optionally substituted with one or more $C_1$ to $C_4$ alkyl groups,
   polyorganosiloxane chains possibly containing one or more oxygen, sulphur and/or nitrogen atoms;
2) the groups X, which may be identical or different, represent a linear or branched $C_1$ to $C_{30}$ alkylenediyl group, optionally containing in its chain one or more oxygen and/or nitrogen atoms;
3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally bearing as substituent one of the following atoms or groups of atoms:
   fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or
4) Y represents a group corresponding to the formula:

in which
   T represents a linear or branched, saturated or unsaturated, $C_3$ to $C_{24}$ trivalent or tetravalent hydrocarbon-based group optionally substituted with a polyorganosiloxane chain, and optionally containing one or more atoms chosen from O, N and S, or T represents a trivalent atom chosen from N, P and Al, and
   $R^5$ represents a linear or branched $C_1$ to $C_{50}$ alkyl group or a polyorganosiloxane chain, optionally comprising one or more ester, amide, urethane, thiocarbamate, urea, urethane, thiourea and/or sulphonamide groups, which may optionally be linked to another chain of the polymer;
5) The groups G, which may be identical or different, represent divalent groups chosen from:

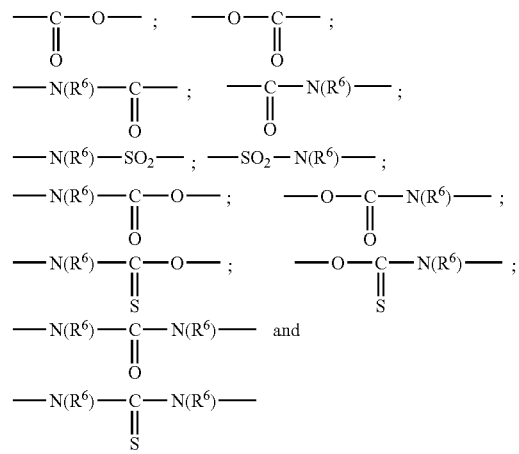

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

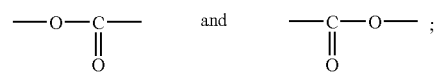

6) n is an integer ranging from 2 to 500 and m is an integer ranging from 1 to 1,000.

3. Composition according to claim 2, in which Y represents a group selected from the group consisting of:
   a) linear $C_1$ to $C_{20}$ alkylene groups, b) $C_{30}$ to $C_{50}$ branched alkylene groups possibly comprising rings and unconjugated unsaturations,
c) $C_5$-$C_6$ cycloalkylene groups,
d) phenylene groups optionally substituted with one or more $C_1$ to $C_{40}$ alkyl groups,
e) $C_1$ to $C_{20}$ alkylene groups comprising from 1 to 5 amide groups,
f) $C_1$ to $C_{20}$ alkylene groups comprising one or more substituents chosen from hydroxyl, $C_3$ to $C_8$ cycloalkane, $C_1$ to $C_3$ hydroxyalkyl and $C_1$ to $C_6$ alkylamine groups,
g) polyorganosiloxane chains of formula:

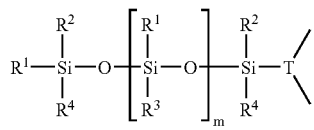

in which $R^1$, $R^2$, $R^3$, $R^4$, T and m are as defined above,
h) polyorganosiloxane chains of formula:

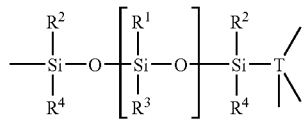

in which $R^1$, $R^2$, $R^3$, $R^4$, T and m are as defined above.

4. Composition according to claim 2, in which X and/or Y represent an alkylene group containing in its alkylene portion at least one of the following elements:
1°) 1 to 5 amide, urea or carbamate groups,
2°) a $C_5$ or $C_6$ cycloalkyl group, and
30°) a phenylene group optionally substituted with 1 to 3 identical or different $C_1$ to $C_3$ alkyl groups, and/or substituted with at least one element chosen from the group consisting of:
a hydroxyl group,
a $C_3$ to $C_8$ cycloalkyl group,
one to three $C_1$ to $C_{40}$ alkyl groups,
a phenyl group optionally substituted with one to three $C_1$ to $C_3$ alkyl groups,
a $C_1$ to $C_3$ hydroxyalkyl group, and
a $C_1$ to $C_6$ aminoalkyl group.

5. Composition according to claim 2, in which Y represents:

in which $R^5$ represents a polyorganosiloxane chain and T represents a group of formula:

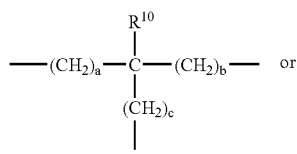

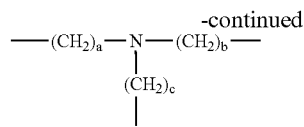

in which a, band c are, independently, integers ranging from 1 to 10, and $R^{10}$ is a hydrogen atom or a group such as those defined for $R^1$, $R^2$, $R^3$ and $R^4$, in claim 2.

6. Composition according to claim 2, in which $R^1$, $R^2$, $R^3$ and $R^4$ represent, independently, a linear or branched $C_1$ to $C_{40}$ alkyl group, a polyorganosiloxane chain or a phenyl group optionally substituted with one to three methyl or ethyl groups.

7. Composition according to claim 2, in which the structuring polymer comprises at least one moiety of formula:

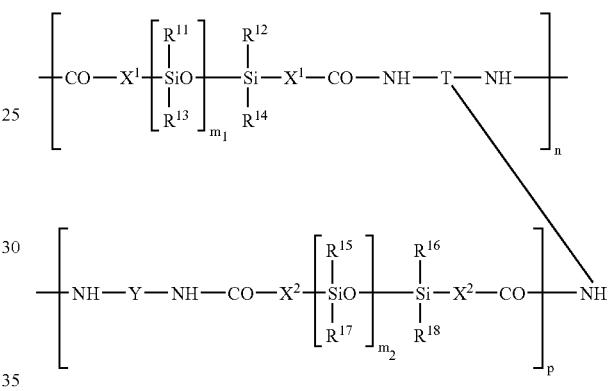

(VII)

in which $X^1$ and $X^2$, which may be identical or different, have the meaning given for X in claim 2, n, Y and T are as defined in claim 2, $R^{11}$ to $R^{18}$ are groups chosen from the same group as $R^1$ to $R^4$ of claim 2, $m_1$ and $m_2$ are numbers in the range from 1 to 1,000, and p is an integer ranging from 2 to 500.

8. Composition according to claim 7, in which:
p is in the range from 1 to 25,
$R^{11}$ to $R^{18}$ are methyl groups,
T corresponds to one of the following formulae:

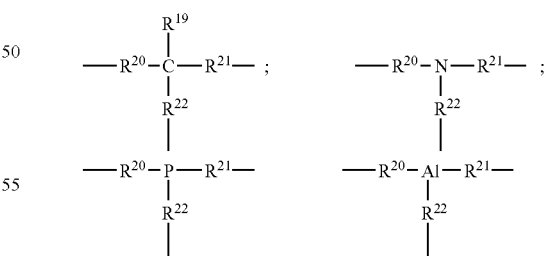

in which $R^{19}$ is a hydrogen atom or a group chosen from the groups defined for $R^1$, to $R^4$, and $R^{20}$, $R^{21}$ and $R^{22}$ are, independently, linear or branched alkylene groups:
$m_1$ and $m_2$ are in the range from 15 to 500,
$X^1$ and $X^2$ represent —$(CH_2)_{10}$—, and
Y represents —$CH_2$—.

9. Composition according to claim 8, in which the structuring polymer comprises at least one moiety of formula:

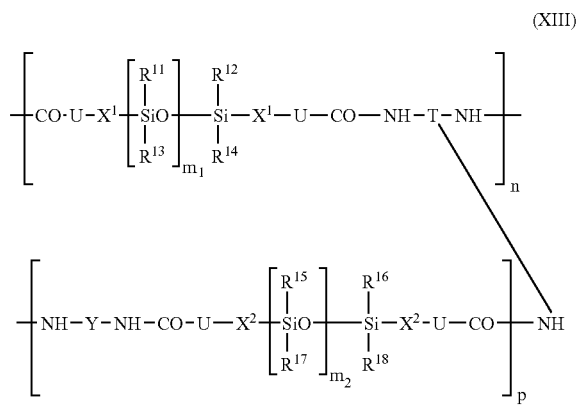

(XIII)

in which $X^1$ and $X^2$, which are identical or different, have the meaning given for X in claim 8, n, Y and T are as defined in claim 8, $R^{11}$ to $R^{18}$ are groups chosen from the same group as $R^1$ to $R^4$ of claim 8, $m_1$ and $m_2$ are numbers in the range from 1 to 1,000, and p is an integer ranging from 2 to 500.

10. Composition according to claim 2, in which the polymer comprises at least one moiety corresponding to the following formula:

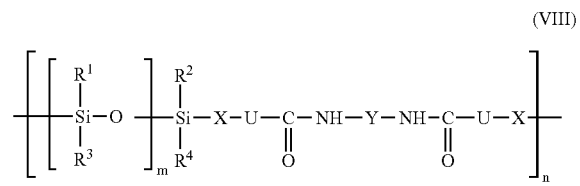

(VIII)

in which $R^1$, $R^2$, $R^3$, $R^4$, X, Y, m and n have the meanings given above for formula (I) in claim 2, and U represents —O— or —NH—, such that:

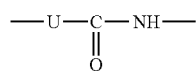

corresponds to a urethane or urea group, or

Y represents a $C_5$ to $C_{12}$ cycloaliphatic or aromatic group that may be substituted with a $C_1$ to $C_{15}$ alkyl group or a $C_5$ to $C_{10}$ aryl group, for example a radical chosen from the methylene-4,4-biscyclohexyl radical, the radical derived from isophorone diisocyanate, 2,4- and 2,6-tolylenes, 1,5-naphthylene, p-phenylene and 4,4′-biphenylenemethane or Y represents a linear or branched $C_1$ to $C_{40}$ alkylene radical or a $C_4$ to $C_{12}$ cycloalkylene radical, or Y represents a polyurethane or polyurea block corresponding to the condensation of several diisocyanate molecules with one or more coupling agents of the diol or diamine type, corresponding to the formula:

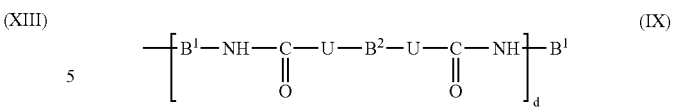

(IX)

in which $B^2$ is a group chosen from the groups given above for Y, U is —O— or —NH— and $B^2$ is chosen from:
- linear or branched $C_1$ to $C_{40}$ alkylene groups, which can optionally bear an ionizable group such as a carboxylic acid or sulphonic acid group, or a neutralizable or quaternizable tertiary amine group,
- $C_5$ to $C_{12}$ cycloalkylene groups, optionally bearing alkyl substituents, for example one to three methyl or ethyl groups, or alkylene,
- phenylene groups that may optionally bear $C_1$ to $C_3$ alkyl substituents, and
- groups of formula:

in which T is a hydrocarbon-based trivalent radical possibly containing one or more hetero atoms such as oxygen, sulphur and nitrogen and $R^5$ is a polyorganosiloxane chain or a linear or branched $C_1$ to $C_{50}$ alkyl chain.

11. Composition according to claim 2, in which the structuring polymer comprises a hydrocarbon-based moiety comprising two groups capable of establishing hydrogen interactions, chosen from ester, amide, sulphonamide, carbamate, thiocarbamate, urea, urethane, thiourea, oxamido, guanamido and biguanidino groups, and combinations thereof.

12. Composition according to claim 1, in which the structuring polymer comprises at least one moiety corresponding to formula (II):

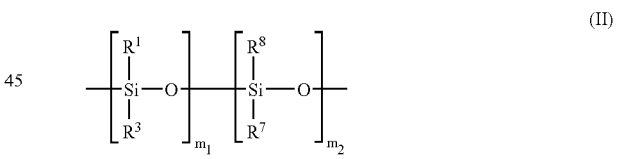

(II)

in which
$R^1$ and $R^3$, which may be identical or different, which may be identical or different, represent a group chosen from:
- linear, branched or cyclic, saturated or unsaturated, $C_1$ to $C_{40}$ hydrocarbon-based groups, possibly containing in their chain one or more oxygen, sulphur and/or nitrogen atoms, and optionally being partially or totally substituted with fluorine atoms,
- $C_6$ to $C_{10}$ aryl groups, optionally substituted with one or more $C_1$ to $C_4$ alkyl groups,
- polyorganosiloxane chains possibly containing one or more oxygen, sulphur and/or nitrogen atoms;

$R^7$ represents a group as defined above for $R^1$ and $R^3$, or represents a group of formula —X-G-$R^9$ in which X represents a linear or branched $C_1$ to $C_{30}$ alkylenediyl group, optionally containing in its chain one or more oxygen and/or nitrogen atoms and G represents divalent groups chosen from:

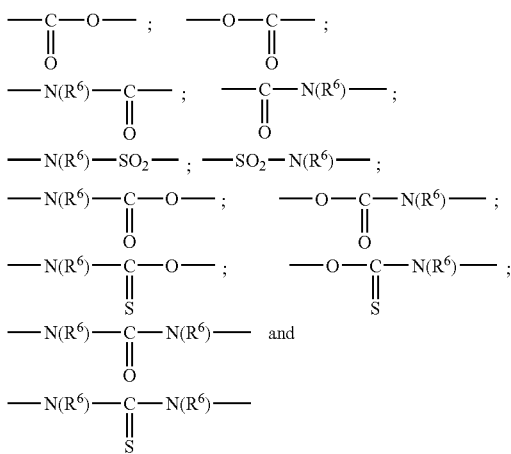

in which $R^6$ represents a hydrogen atom or a linear or branched $C_1$ to $C_{20}$ alkyl group, on condition that at least 50% of the groups $R^6$ of the polymer represents a hydrogen atom and that at least two of the groups G of the polymer are a group other than:

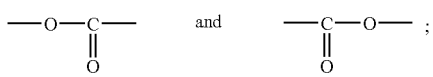

and $R^9$ represents a hydrogen atom or a linear, branched or cyclic, saturated or unsaturated, $C_1$ to $C_{50}$ hydrocarbon-based group optionally comprising in its chain one or more atoms chosen from O, S and N, optionally substituted with one or more fluorine atoms and/or one or more hydroxyl groups, or a phenyl group optionally substituted with one or more $C_1$ to $C_4$ alkyl groups, $R^8$ represents a group of formula —X-G-$R^9$ in which X, G and $R^9$ are as defined above, $m_1$ is an integer ranging from 1 to 998, and $m_2$ is an integer ranging from 2 to 500.

13. Composition according to claim 1, in which the polymer comprises at least one moiety of formula (III) or (IV):

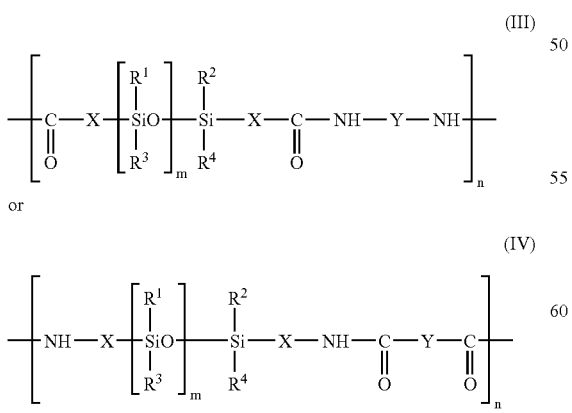

in which $R^1$, $R^2$, $R^3$, and $R^4$ may be identical or different, represent a group chosen from:

linear, branched or cyclic, saturated or unsaturated, $C_1$ to $C_{40}$ hydrocarbon-based groups, possibly containing in their chain one or more oxygen, sulphur and/or nitrogen atoms, and optionally being partially or totally substituted with fluorine atoms, $C_6$ to $C_{10}$ aryl groups, optionally substituted with one or more $C_1$ to $C_4$ alkyl groups, polyorganosiloxane chains possibly containing one or more oxygen, sulphur and/or nitrogen atoms;

2) the groups X, which may be identical or different, represent a linear or branched $C_1$ to $C_{30}$ alkylenediyl group, optionally containing in its chain one or more oxygen and/or nitrogen atoms;

3) Y is a saturated or unsaturated, $C_1$ to $C_{50}$ linear or branched divalent alkylene, arylene, cycloalkylene, alkylarylene or arylalkylene group, optionally comprising one or more oxygen, sulphur and/or nitrogen atoms, and/or optionally bearing as substituent one of the following atoms or groups of atoms:

fluorine, hydroxyl, $C_3$ to $C_8$ cycloalkyl, $C_1$ to $C_{40}$ alkyl, $C_5$ to $C_{10}$ aryl, phenyl optionally substituted with 1 to 3 $C_1$ to $C_3$ alkyl groups, $C_1$ to $C_3$ hydroxyalkyl and $C_1$ to $C_6$ aminoalkyl, or 4) Y represents a group corresponding to the formula:

in which

T represents a linear or branched, saturated or unsaturated, $C_3$ to $C_{24}$ trivalent or tetravalent hydrocarbon-based group optionally substituted with a polyorganosiloxane chain, and optionally containing one or more atoms chosen from O, N and S, or T represents a trivalent atom chosen from N, P and Al, and $R^5$ represents a linear or branched $C_1$ to $C_{50}$ alkyl group or a polyorganosiloxane chain, optionally comprising one or more ester, amide, urethane, thiocarbamate, urea, urethane, thiourea and/or sulphonamide groups, which may optionally be linked to another chain of the polymer;

n is an integer ranging from 2 to 500; and m is an integer ranging from 1 to 1,000.

14. Composition according to claim 1, in which the structuring polymer comprises at least one moiety of formula:

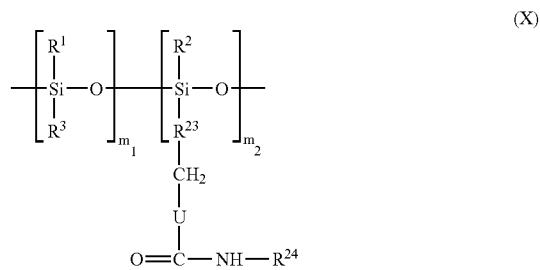

in which $R^1$, $R^2$, $R^3$, $m_1$ and $m_2$ have the meanings given above for formula (I), U represents O or NH, $R^{23}$ represents a $C_1$ to $C_{40}$ alkylene group, optionally comprising one or more hetero atoms chosen from O and N, or a phenylene group, and $R^{24}$ is chosen from linear, branched or cyclic, saturated or unsaturated $C_1$ to $C_{50}$ alkyl groups, and phenyl groups optionally substituted with one to three $C_1$ to $C_3$ alkyl groups.

15. Composition according to claim 1, in which the structuring polymer comprises a hydrocarbon-based moiety comprising two groups capable of establishing hydrogen interactions, chosen from ester, amide, sulphonamide, carbamate, thiocarbamate, urea, urethane, thiourea, oxamido, guanamido and biguanidino groups, and combinations thereof.

16. Composition according to claim 1, in which the at least one structuring polymer represents from 0.5% to 80% relative to the total weight of the composition.

17. Composition according to claim 1, wherein said at least one structuring polymer has a softening point greater than 50° C.

18. Composition according to claim 1, wherein said at least one structuring polymer has a softening point of less than 150° C.

19. Composition according to claim 1, wherein said at least one structuring polymer has a softening point ranging from 70°C. to 130° C.

20. Composition according to claim 1, wherein said at least one structuring polymer has a weight-average molecular weight ranging from 500 to 300,000.

21. Composition according to claim 1, wherein said composition has a hardness ranging from 30 to 300 gf.

22. Composition according to claim 21, wherein said at least one oil is a hydrocarbon chosen from linear and branched, volatile and non-volatile hydrocarbons of synthetic and mineral origin.

23. Composition according to claim 1, wherein said composition has a hardness ranging 30 to 200 gf.

24. Composition according to claim 1, wherein said composition is in the form of a rigid gel.

25. Composition according to claim 1, wherein said composition is anhydrous.

26. The composition according to claim 25, wherein said structuring polymer has the following formula:

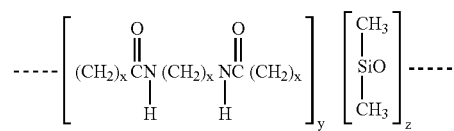

where x, which may be the same or different, is from 1-100 and the ratio y/z is from 1-10.

27. The composition according to claim 26, wherein said oil is a dimethicone.

28. The composition according to claim 27, wherein said composition is in the form of a rigidified or solid gel that is reversible thermally and/or upon the application of shear.

29. The composition according to claim 26, wherein said oil is a silicone oil.

30. The composition according to claim 29, wherein said composition is in the form of a rigidified or solid gel that is reversible thermally and/or upon the application of shear.

31. The composition according to claim 1, further comprising a colorant.

32. The composition of claim 1, further comprising a wax.

33. The composition according to claim 1, further comprising polyethylene.

34. A method comprising applying to keratin material the composition of claim 1.

35. The composition according to claim 1, wherein said composition is in the form of an emulsion.

36. The composition according to claim 1, wherein the silicone elastomer particles are functionalized with fluoroalkyl groups.

37. The composition according to claim 1, wherein the silicone elastomer particles are functionalized with phenyl groups.

* * * * *

UNITED STATES PATENT AND TRADEMARK OFFICE
CERTIFICATE OF CORRECTION

PATENT NO. : 7,329,699 B2  Page 1 of 1
APPLICATION NO. : 10/617048
DATED : February 12, 2008
INVENTOR(S) : Terry Van Liew et al.

It is certified that error appears in the above-identified patent and that said Letters Patent is hereby corrected as shown below:

Column 29, line 37, "30°'" should read --3°--.

Column 30, after line 62, insert the following formula:

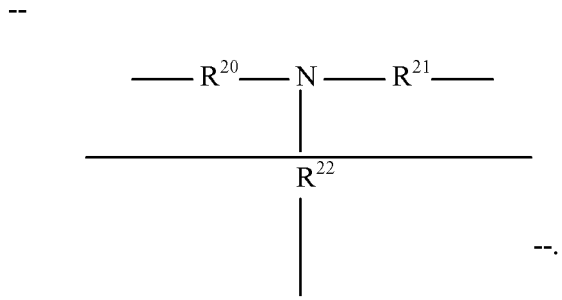

Column 32, line 10, "C," should read --$C_1$--;
line 12, "suiphonic" should read --sulphonic--.

Signed and Sealed this

Fifth Day of August, 2008

JON W. DUDAS
*Director of the United States Patent and Trademark Office*